United States Patent [19]
Nesto

[11] Patent Number: 5,957,911
[45] Date of Patent: *Sep. 28, 1999

[54] LEFT CORONARY GUIDING CATHETER

[75] Inventor: Richard W. Nesto, Weston, Mass.

[73] Assignee: Advanced Cardiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/588,905

[22] Filed: Jan. 19, 1996

Related U.S. Application Data

[63] Continuation of application No. 08/146,451, Nov. 1, 1993, abandoned, which is a continuation of application No. 07/826,744, Jan. 28, 1992, abandoned.

[51] Int. Cl.⁶ .................................................. A61M 25/00
[52] U.S. Cl. .......................................... 604/532; 600/435
[58] Field of Search .............................. 604/95, 280, 281, 604/264, 523, 532; 128/656–658; 600/433–435

[56] References Cited

U.S. PATENT DOCUMENTS

| | | | |
|---|---|---|---|
| 3,935,857 | 2/1976 | Co | 128/2.05 |
| 4,033,331 | 7/1977 | Guss et al. | 128/2 M |
| 4,177,836 | 10/1978 | Erikson | 128/2.05 R |
| 4,385,635 | 5/1983 | Ruiz | 128/658 |
| 4,430,083 | 2/1984 | Ganz et al. | 128/772 |
| 4,516,972 | 5/1985 | Samson | 604/282 |
| 4,547,193 | 10/1985 | Rydell | 604/282 |
| 4,586,923 | 5/1986 | Gould et al. | 604/93 |
| 4,636,346 | 1/1987 | Gold et al. | 264/139 |
| 4,739,768 | 4/1988 | Engelson | 128/658 |
| 4,747,840 | 5/1988 | Ladika et al. | 604/281 |
| 4,759,748 | 7/1988 | Reed et al. | 604/93 |
| 4,777,951 | 10/1988 | Cribier et al. | 128/344 |
| 4,784,639 | 11/1988 | Patel et al. | 604/53 |
| 4,808,164 | 2/1989 | Hess | 604/95 |
| 4,813,930 | 3/1989 | Elliott | 604/53 |
| 4,817,613 | 4/1989 | Jaraczewski et al. | 128/658 |
| 4,820,349 | 4/1989 | Saab | 604/101 |
| 4,822,345 | 4/1989 | Danforth | 604/282 |
| 4,886,506 | 12/1989 | Loregren et al. | 604/280 |
| 4,976,691 | 12/1990 | Sahota | 604/280 |
| 5,044,369 | 9/1991 | Sahota | 604/280 |
| 5,045,072 | 9/1991 | Castillo et al. | 604/280 |
| 5,122,125 | 6/1992 | Deuss | 604/280 |
| 5,163,921 | 11/1992 | Feiring | 604/281 |

FOREIGN PATENT DOCUMENTS

| | | |
|---|---|---|
| 323738 | 7/1989 | European Pat. Off. . |
| 334640 | 9/1989 | European Pat. Off. . |

OTHER PUBLICATIONS

Catheterization and Cardiovascular Diagnosis No. 24, 1991, pp. 144–148, Nesto, R.W. "Performance Characteristics of a New Shape of Guiding Catheter for PTCA of the Left Coronary Artery".

"USCI Positrol II & Nycore ™ Cardiovascular Catheters" 1990.

"PTCA in Perspective"Guiding Catheters, USCI/Technical Perspective pp. 23–42, 1986.

"Mechanics of Selective Coronary Artery Catheterization via Femoral Approach" Kurt Amplatz et al, pp. 1040–1047, Dec. 1967.

*Primary Examiner*—Mark Bockelman
*Attorney, Agent, or Firm*—Heller Ehrman White & McAuliffe

[57] ABSTRACT

A left coronary guide catheter having primary, secondary and tertiary curves formed therein to facilitate insertion and positioning of the distal tip of the catheter within the left coronary ostium. The distal portion of the catheter may be formed of material which is softer than the remainder of the catheter.

10 Claims, 4 Drawing Sheets

LEFT CORONARY GUIDING CATHETER

This is a continuation of Ser. No. 08/146,451 filed Nov. 1, 1993, abandoned, which is a continuation of Ser. No. 07/825,744 filed Jan. 22, 1992 which is abandoned.

FIELD OF THE INVENTION

The present invention relates generally to medical equipment and more particularly to an improved left coronary artery guide catheter for use in the performance of medical procedures such as coronary angiography and angioplasty.

BACKGROUND OF THE INVENTION

Various types of cardiovascular catheters are known in the prior art. Such prior art cardiovascular catheters include certain coronary artery catheters which are specifically sized and configured to be percutaneously inserted and advanced through the vasculature into the ostia of the left or right main coronary artery. Such coronary artery catheters include (a) coronary angiography catheters which are typically used to inject radiographic contrast medium directly into the coronary vasculature and (b) coronary guiding catheters which are typically used to guide the advancement of a guidewire and/or a second catheter (e.g. a balloon angioplasty catheter) into a specific coronary artery.

The primary application for coronary "guiding" catheters is presently in the performance of percutaneous transluminal coronary angioplasty (PTCA) procedures. Such PTCA procedures routinely involve the initial percutaneous insertion of a 0.35-inch guidewire into a peripheral artery (e.g. a femoral artery) with subsequent advancement of the distal tip of the guidewire into the thoracic aorta. A coronary guiding catheter is then advanced over the preinserted guidewire to a point near the origin of the coronary artery at which point the 0.035-inch guidewire is removed. The distal tip of the "guiding" catheter is then inserted within the desired (i.e. right or left) coronary ostium. A smaller diameter balloon angioplasty catheter is then advanced over a smaller diameter (typically 0.10–0.18 inches), through the lumen of the guiding catheter, to a point where the balloon is within the distal aspect of the guiding catheter. The guidewire is then further advanced out of and beyond the distal tip of the guiding catheter such that the distal tip of the guidewire passes into, through, or around the occlusive coronary lesion to be treated is located. Once the guidewire has been passed through or across the occlusive lesion, the operator then further advances the balloon dilation catheter over the guidewire to a point where the balloon has become positioned at the stenotic lesion. The balloon dilatation angioplasty procedure is then accomplished by repetitive inflation and deflation of the balloon. After the angioplasty has been completed, the balloon catheter and guidewire are withdrawn, leaving the coronary guiding catheter in place. Roentgenographic contrast medium may then be injected through the coronary guiding catheter to determine whether the angioplasty procedure has successfully restored patency of the diseased vessel.

Those skilled in the art will appreciate that, during the insertion and manipulation of an angioplasty catheter, the coronary guiding catheter through which the angioplasty catheter is inserted must provide sufficient guidance and "backup" to prevent bending or kinking of the angioplasty catheter as it is advanced and/or manipulated through the stenotic lesion. The guide catheter must provide sufficient stability of position to enable the balloon catheter to follow the guidewire despite tortuosity of the coronary artery and the severity of the target lesion. Also, it is desirable that the distal tip of the guiding catheter be directly inserted into the main coronary artery in a manner that will not interfere with subsequent manipulation or torquing of the guidewire and/or angioplasty catheter into a desired branch of such main coronary artery. Additionally, it is desirable that the "guiding" catheter be constructed in a manner that will prevent the distal tip of the catheter from creeping or inadvertently advancing an inordinate distance into the main coronary artery as such "creeping" or inadvertent advancement of the guiding catheter tip may interfere with or complicate subsequent extraction and withdrawal of the guiding catheter.

Examples of cardiovascular catheters which are purported to be sized and/or configured and/or constructed for insertion into a coronary artery are included in the following U.S. Pat. Nos. 4,739,768 (Engelson); 4,385,635 (Ruiz); 4,813,930 (Elliott); 4,759,748 (Reed); 4,817,613 (Jaraczewski et al.); 4,586,923 (Gould et al.); 4,636,346 (Gold et al.); 4,033,331 (Guss et al.); 4,784,639 (Patel); 4,117,836 (Erikson); 4,822,345 (Danforth); 3,935,857 (Co); 4,516,972 (Samson); 4,547,193 (Rydell); 4,747,840 (Ladika et al.); 4,777,951 (Cribier et al.); and 4,808,164 (Hess). Although many types of coronary artery catheters exist in the prior art, no single coronary artery catheter has been found to be universally optimal for use as a "guiding" catheter in the performance of all coronary angioplasty procedures. Accordingly, there remains a need in the art for improved coronary guiding catheters for use in guiding guidewires, balloon angioplasty devices and the like into a specific coronary artery.

SUMMARY OF THE INVENTION

The present invention overcomes some or all of the shortcomings of the prior art by providing an improved left coronary artery guiding catheter which is a) specifically configured and constructed to facilitate ease of insertion into the left coronary ostium, b) sufficiently rigid and appropriately constructed to provide adequate guiding support or back up during insertion and manipulation of a coronary balloon angioplasty catheter therethrough and c) specifically configured at its distal end to minimize or deter "creeping" or undesired further advancement into the left main coronary artery while the operative angioplasty procedure is being conducted.

The left coronary artery catheter of the present invention has previously been subjected to experimental use in patients. The specific shape and construction of the catheter of the present invention, as well as the catheterization technique by which the catheter of the present invention is utilized, is described in Nesto, R. W., "Performance Characteristics of a New Shape of Guiding Catheter for PTCA of the Left Coronary Artery", *Catheterization and Cardiovascular Diagnosis*, 24:144–148 (1991), the entirety of which is expressly incorporated herein by reference.

In accordance with the invention, there is provided a left coronary artery catheter comprising an elongate tubular catheter body formed of flexible material such as flexible nylon (PEBAX™, Atochimie, Courbevoie, Hauts-Ve-Sine, FRANCE). The distal portion of the catheter includes three (3) curves—a "primary" curve, a "secondary" curve and a "tertiary" curve. The "primary" curve of 30° +/− 15° is formed near the distal tip of the catheter. A secondary curve of 70° +/− 15° is formed proximal to the primary curve. A "tertiary" curve of 100° +/− 15° is formed proximal to the secondary curve. The distance between the secondary and tertiary curves is preferably between 1.5 cm and 3 cm depending on the size and specific anatomy of the patient.

Further in accordance with the invention, the distal tip may be formed of material which is softer than the remainder of the catheter body. In a presently preferred embodiment, the distal tip of the catheter is made of PEBAX™ 3 which has a Shore D durometer hardness of 33+/−5 while the remainder of the catheter is formed of PEBAX™ 6 which has a Shore D durometer hardness of 63+/−5.

Further in accordance with the invention, several specific sizes of the guide catheter may be prepared to accommodate anatomic and size variations among patients. The presently preferred sizings of the specific catheters include four (4) incremental catheter sizes defined by incremental variations in the length of the catheter body from the midpoint of the secondary curved to the midpoint of the tertiary curve of 1.5, 2.0, 2.5 and 3.0 cm respectively.

Further aspects, objects and advantages of the invention will become apparent to those skilled in the art upon reading and understanding the following detailed description and the accompanying drawings.

DETAILED DESCRIPTION OF THE PREFERRED EMBODIMENT

The following description and the accompanying drawings are provided for purposes of illustrating and describing a presently preferred embodiment of the invention and are not intended to limit the scope of the invention in any way.

Figure 1:
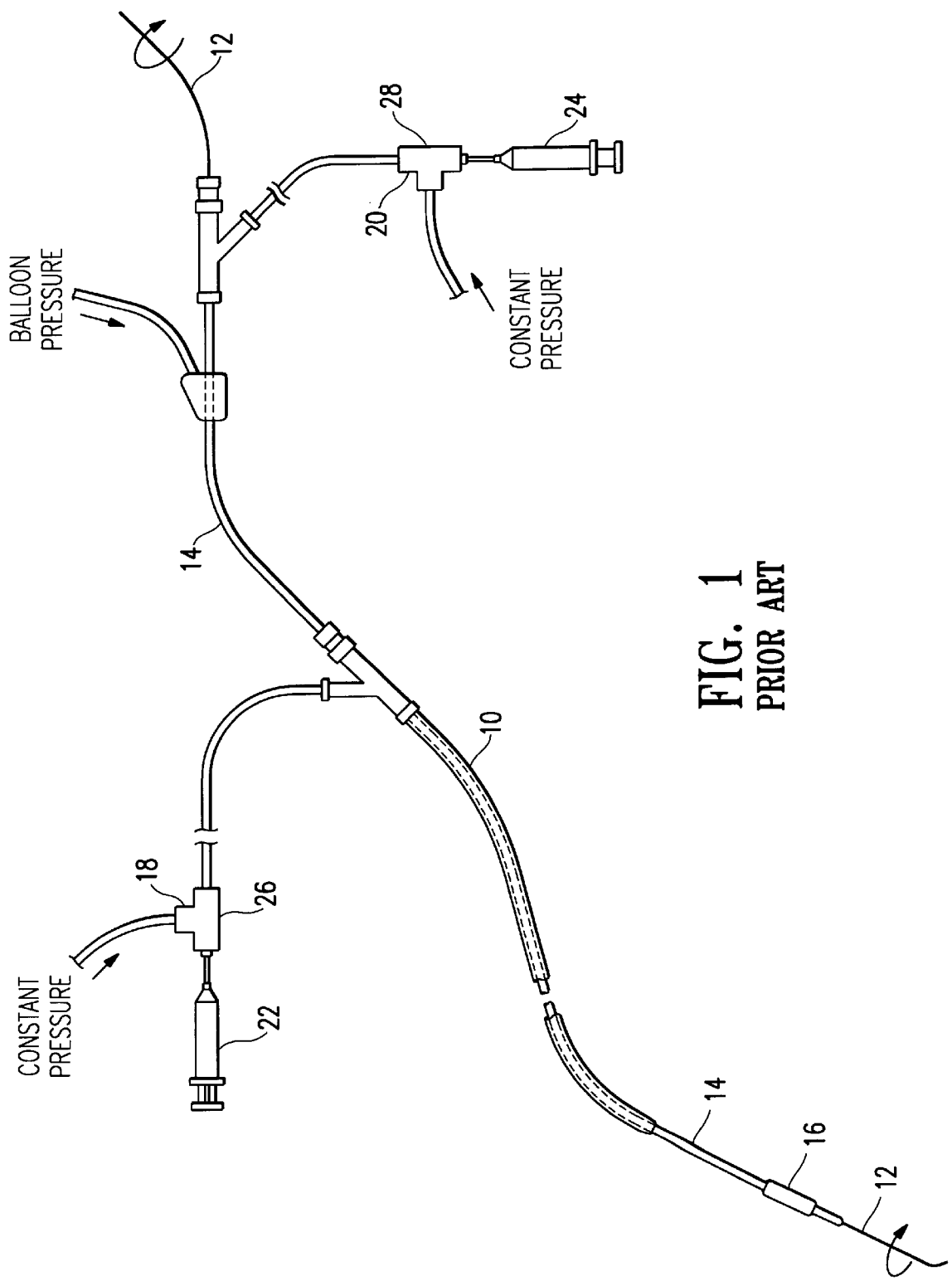
FIG. 1 is a schematic diagram of a typical transluminal coronary artery balloon angioplasty system.

Referring to the drawings, FIG. 1 is a schematic showing of a typical transluminal balloon angioplasty system of the prior art. As shown, the typical balloon angioplasty system comprises a flexible coronary guiding catheter 10 which is percutaneously inserted into an artery (e.g. the femoral artery) and subsequently advanced to a point where the distal tip of the guiding catheter 10 resides within the ostium of a target coronary artery. Thereafter, a thin flexible guidewire 12 is advanced through the lumen of the guiding catheter 10 such that the distal end of the guidewire 12 advances out of and beyond the distal tip of the guiding catheter 10, reaching a point adjacent or within the offending stenotic lesion. Thereafter, a balloon angioplasty catheter 14 is advanced over the guidewire to a point where the angioplasty balloon 16 resides adjacent the offending stenotic lesion. The angioplasty balloon 16 is then repetitively inflated and deflated to bring about dilation of the stenotic lesion, thereby opening the previously occluded coronary artery.

Constant pressure ports 18 and 20 are provided for passing constant pressure saline solution through the guiding catheter 10 and balloon catheter 14 respectively. The passage of such constant pressure saline solution through the guiding catheter 10 and balloon catheter 14 is intended to prevent backflow of blood through the catheter and to permit periodic flushing of the catheter.

Attendant syringes 22 and 24 are mounted on manifolds 26, 28 for injection of radiographic contrast media or certain medicaments through the guiding catheter 10 or balloon catheter 14 during the operative procedure.

The typical coronary guiding catheter 10 comprises an elongate flexible plastic tube having preformed curves formed in the distal portion thereof to facilitate advancement of the distal portion of the catheter through the aortic arch and placement of the distal tip of the catheter within a desired coronary ostium. The curvatures formed in the distal portion of the guiding catheter will differ depending on which coronary artery the catheter is intended to access.

During the initial insertion of the coronary guiding catheter 10, it is common practice for the operator to grasp the exteriorized proximal portion of the catheter 10 and to twist, torque, push and pull the catheter as necessary to guide the distal tip of the catheter into its desired position within the target coronary ostium. Accordingly, it is desirable that the guiding catheter 10 have sufficient structural rigidity to transmit torsional rotation of the catheter from the proximal end thereof to the distal end thereof. Moreover, during insertion of the guiding catheter 10, it is common for the distal tip of the catheter to rub against the luminal surfaces of the blood vessels through which it is advanced and to repeatedly probe or bump against the tissues surrounding the coronary ostia while the operator is endeavoring to guide and insert the distal tip of the catheter in the desired ostium. Thus, it is desirable that the distal tip of the coronary guiding catheter 10 be sufficiently soft or flexible to avoid unnecessary trauma to the blood vessel walls and/or coronary ostia during placement thereof.

Figure 2:
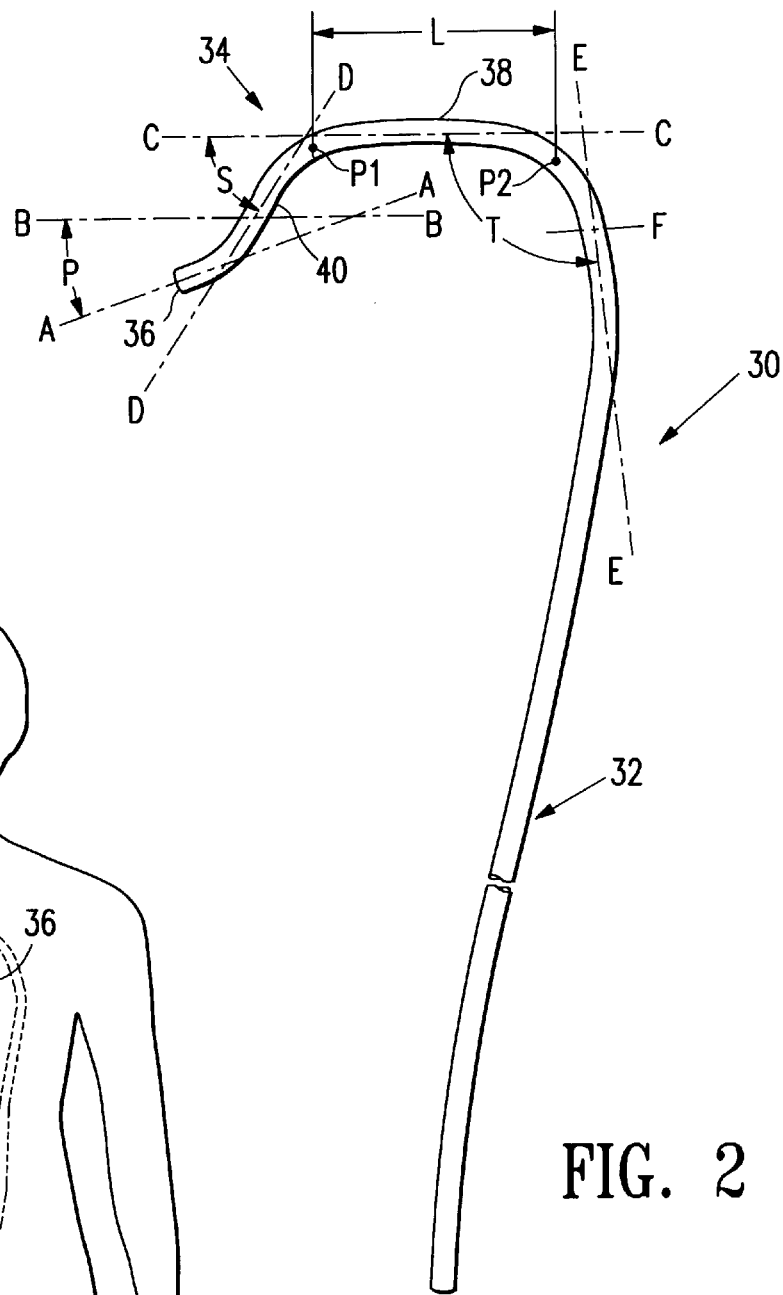
FIG. 2 is a perspective view of a left coronary artery guide catheter of the present invention.
Figure 5:
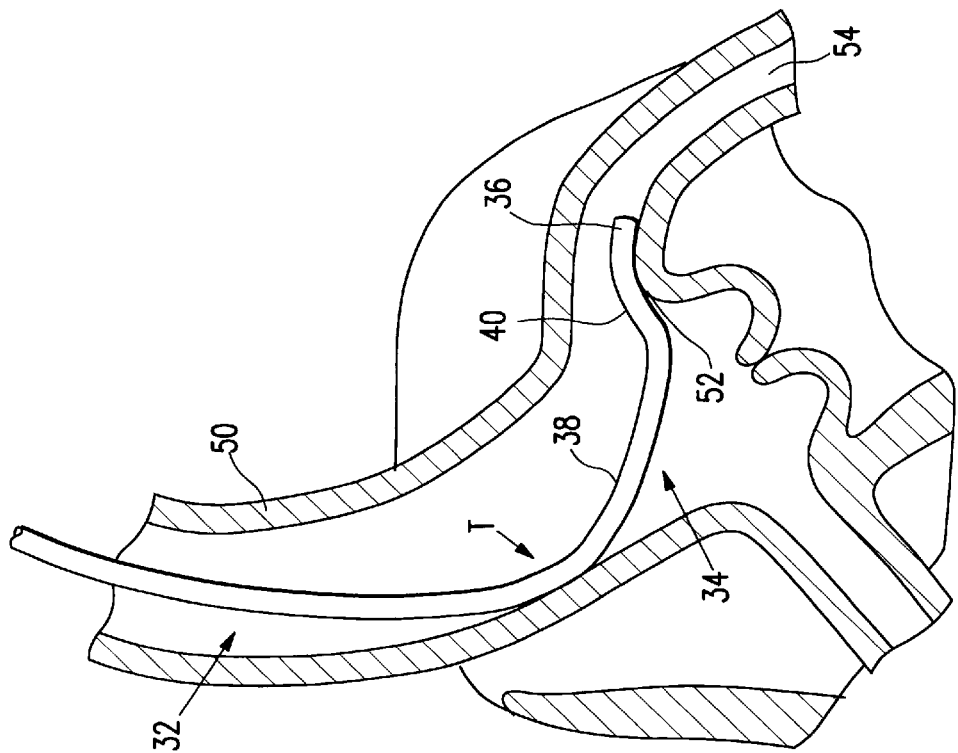
FIG. 5 is an enlarged cross-sectional view of segment 5 of FIG. 4.
Figure 4:
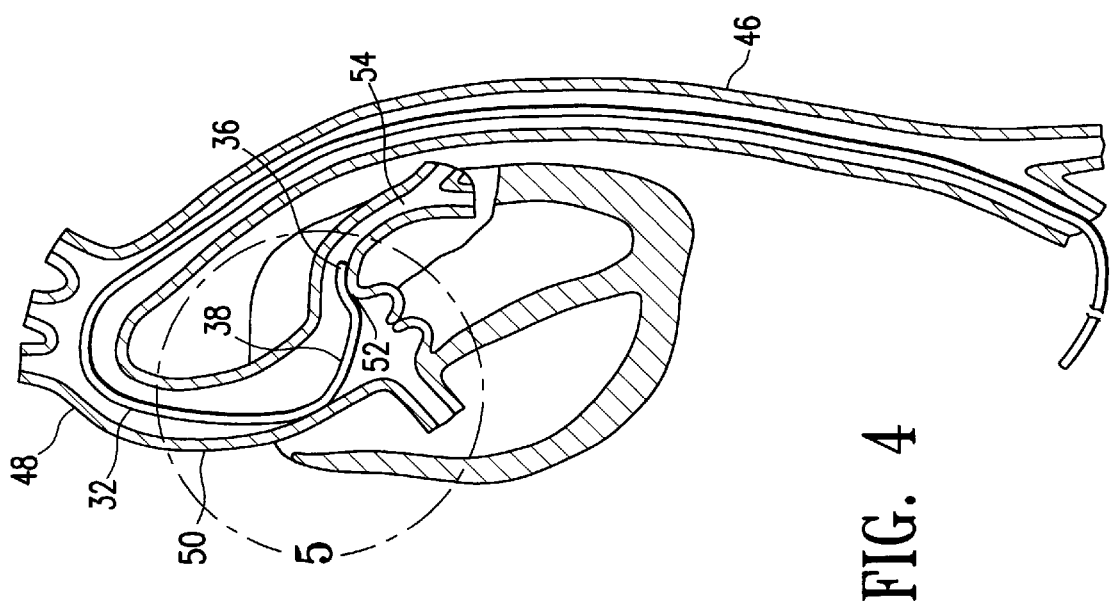
FIG. 4 is a cross-sectional view of the heart and aorta of a human being having a left coronary artery guide catheter of the present invention operatively positioned therein.
Figure 6:
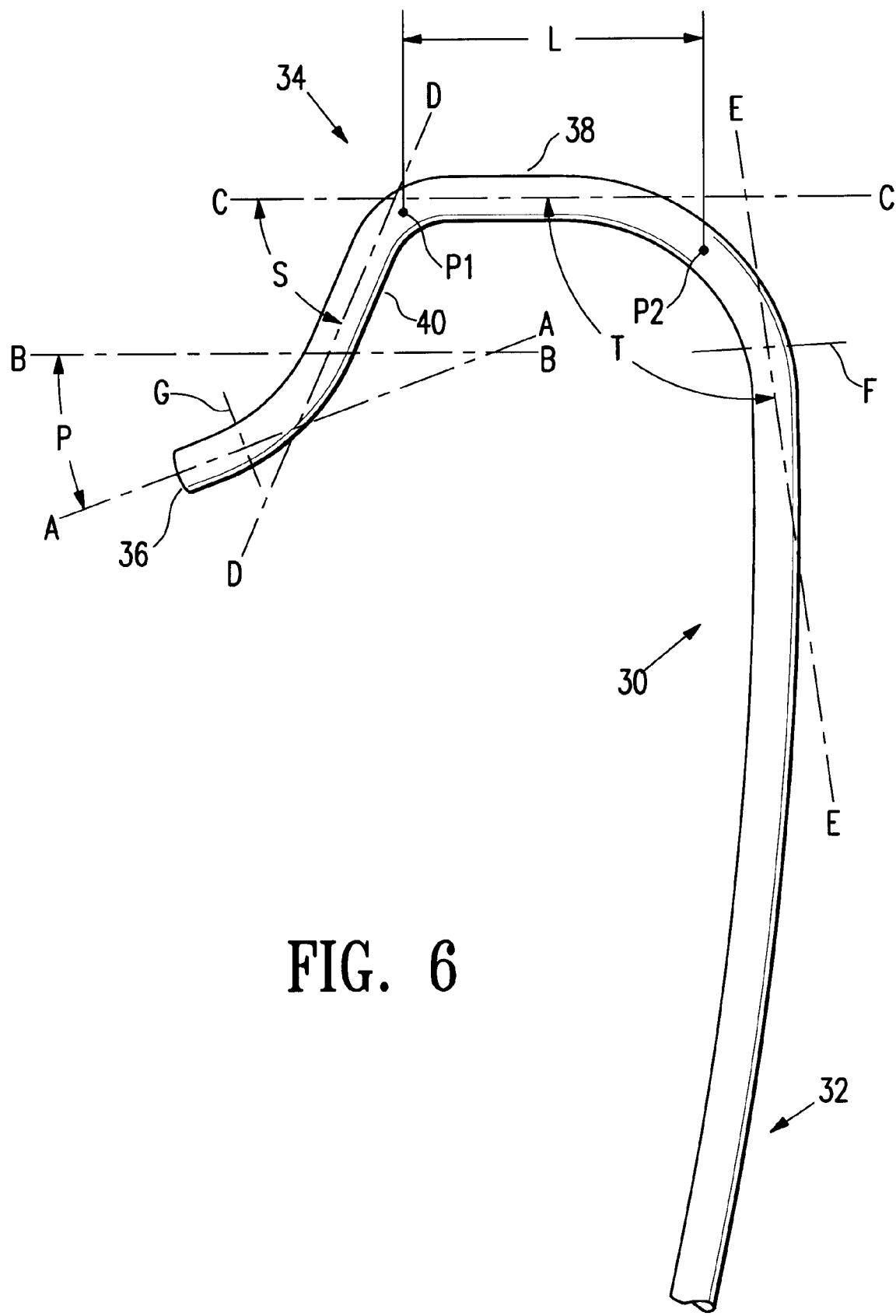
FIG. 6 is an enlarged view of the distal portion of a left coronary artery guide catheter of the present invention showing the specific shape and configuration of the primary, secondary and tertiary bends formed therein.

The present invention is particularly applicable to the coronary guiding catheter 10, as illustrated in FIG. 1, and more particularly to a left coronary artery guiding catheter 30 which is specifically configured and constructed to facilitate ease of insertion into the left coronary ostium. FIGS. 2 and 6 show the left coronary artery guiding catheter 30 of the present invention while FIGS. 4 and 5 show preferred intracorporeal operative placement of the catheter 30 in accordance with the present invention.

In general, the left coronary artery catheter 30 of the present invention comprises an elongate tubular catheter body having a proximal portion 32 which extends to the line F and a distal portion 34. The distal portion 34 of the catheter 30 includes three (3) curves. Specifically, the distal portion 34 defines a "primary" curve P, a "secondary" curve S and a "tertiary" curve T. The primary curve P is formed near a distal tip 36 of the catheter 30 which extends distally beyond the line G as seen in FIG. 6, while the secondary curve S is formed proximal to the primary curve P. The tertiary curve T is formed proximal to the secondary curve S and is separated therefrom by an intermediate section 38 of the distal portion 34. In the preferred embodiment, the primary curve P is approximately 30° +/− 15° and is defined by a first axis A—A extending axially through the distal tip 36 and a second axis B—B which is substantially parallel to a third axis C—C extending axially through the intermediate section 38. The secondary curve S is preferably 70° +/− 15° and is defined by the third axis C—C and a fourth axis D—D extending axially through a distal section 40 of the catheter 30 which is immediately adjacent the distal tip 36. The tertiary curve T is preferably 100° +/− 15° and is defined by the third axis C—C and a fifth axis E—E which extends axially through the proximal portion 32 of catheter 30 immediately adjacent the tertiary curve T.

As seen in FIGS. 2 and 6, the intermediate section 38 lies between the secondary curve S and tertiary curve T. In the preferred embodiment, the distance L between the secondary S and tertiary T curves, i.e. the length of intermediate section 38, is preferably between 1.5 cm and 3 cm, depending on the size and the specific anatomy of the patient 42. Importantly, the distance L is measured between a midpoint P1 of secondary curve S and a midpoint P2 of the tertiary curve T. Advantageously, several specific sizes of the guide catheter 30 may be prepared to accommodate anatomic and size variations among patients. In this respect, the presently preferred sizings of the specific catheters include four (4) incremental or catheter sizes defined by incremental variations in the distance L separating the midpoint P1 of the secondary curve S from the midpoint P2 of the tertiary curve T. These incremental variations for the distance L are 1.5, 2.0, 2.5 and 3.0 cm, respectively. However, it will be recognized that other incremental variations in the distance L may be utilized.

The left coronary artery catheter 30 is preferably formed of flexible material such as flexible nylon (PEBAX™, Atochimie, Courbevoie, Hauts-Ve-Sine, FRANCE). Additionally, the distal tip 36 may be formed of material which is softer than the remainder of the catheter body. In the preferred embodiment, the distal tip 36 of the catheter 30 is made of PEBAX™ 3 which has a Shore D durometer hardness of 33+/−5 while the remainder of the catheter 30 is formed of PEBAX™6 which has a Shore D durometer hardness of 63+/−5. At 37° Celsius, PEBAX™ 6 has a flexural modulus of about 30,000 psi while the PEBAX™ 3 has a flexural modulus of about 5,000 psi.

Optionally, reinforcement members such as stainless steel braiding may be formed within or around some or all of the catheter 30 to enhance the torque transmission capability of the catheter 30.

Figure 3:
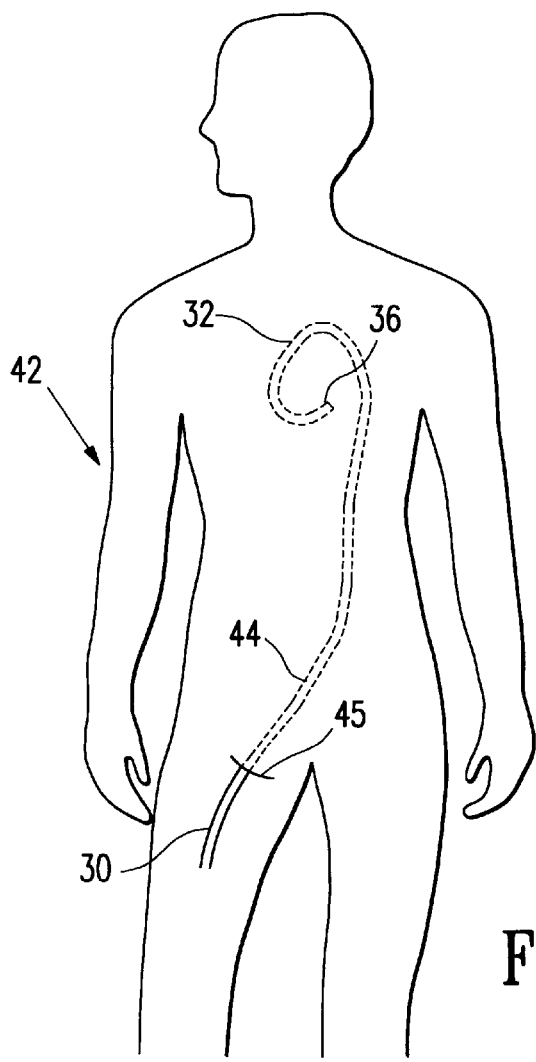
FIG. 3 is an illustration of a human being having a left coronary artery guide catheter of the present invention inserted through the right femoral artery and advanced through the aorta to an operative position wherein the distal tip of the guide catheter is disposed within the ostium of the left coronary artery.

Referring to FIGS. 3–5, the left coronary artery guiding catheter 30 of the present invention is typically inserted into a femoral artery 44 of the patient 42 via an incision 46 and advanced in a retrograde fashion through the descending aorta 46, through the aortic arch 48 and down the ascending aorta 50 to a position where the distal section 40 and distal tip 36 becomes inserted into the ostium 52 of the left coronary artery 54. The proximal portion 32 of the catheter 30 possesses sufficient elasticity so as to correspond to the anatomical configuration of the aortic arch 48 and resides therewithin without exerting excessive pressure or excessive rubbing against the walls of the aortic arch 48.

As shown in FIGS. 2 and 4–6, the catheter body 32 has a substantially constant outer diameter over its entire length.

[The technique required to engage the left coronary ostium with the NL catheter resembles the approach used to engage the left system with an AL catheter]. With reference to FIGS. 4–6, the [The NL] catheter 30 is advanced to the ascending aorta over a guidewire (FIG. [2]ZA). The catheter 30 will reach the aortic valve with its distant tip 38 pointing downward toward the base of the left sinus of Valsalva below the takeoff of the left main (LM) coronary artery 54. The "heel" or the tertiary curve (T) of the catheter 30 is positioned high in the proximal aortic root. The catheter 30 occupies the entire diameter of the aortic root. Advancement with some counterclockwise rotation will direct its tip 38 to ride up the wall of the sinus of Valsalva until it reaches and engages the ostium of the LM coronary artery 54. The tip 38 of the [NL guide] catheter 30 is angulated and will seek the ostium as the catheter is gently advanced. During this maneuver the portion of the catheter between the secondary (S) and tertiary (T) curves may be positioned on the aortic valve, but once engaged the catheter is pulled back so that its heel is positioned against the aortic wall, usually above the point at which the coronaries originate (FIG. [2]7B). Occasionally, the tip 38 may "jump" past the LM orifice when advancing the guiding catheter 30. Retraction of the guide catheter 30 just at the point when the tip 38 moves above the [LM] left main coronary artery 34 will usually direct it into the ostium as the catheter seeks to retain its preformed shape. Occasionally when attempting engagement of the left main 54 [LM], the catheter 30 may prolapse into the left ventricle. The left main coronary artery 54 may be engaged with less difficulty on a second or third attempt. Repeated prolapse into the left ventricle or inability to advance the [NL] catheter 30 toward the left coronary 54 indicates that a smaller size [NL] catheter 30 should be used. Once properly seated, slight retraction of the catheter 30 will usually direct the tip 38 towards the left circumflex (LCX), whereas advancement will direct the tip 38 in a superior direction toward the left anterior descending (LAD) coronary artery (FIG. [2]7B). The technique required to withdraw [an NL] the catheter 30 initially moves [resembles the technique used to disengage a JL catheter from the left ostium.] [The] the heel CO of the [NL] comes] catheter. off the aortic wall allowing the tip 38 to become disengaged without paradoxical advancement of the catheter tip 38 [advancement] or "tenting" of the LM (FIG. [2]7C).

In the preferred embodiment, the tertiary curve T is shaped to facilitate passage of the distal section 40 and distal tip 36 into the ostium 52 of the left coronary artery 54 as shown in FIGS. 4 and 5. In this respect, the catheter 30 is manipulated in a manner such that the tertiary curve T is directly abutted against the inner wall of the ascending aorta 50. The secondary curve S and primary curve P are specifically configured to orient the distal section 40 and distal tip 36 within the left coronary artery 54 and maintain the distal tip 36 therewithin via the abutment thereof against the inner wall of the left coronary artery 54. Importantly, the distance L separating the midpoints P1, P2 of the secondary curve S and tertiary curve T and the length of the distal tip 36 are specifically selected to correspond to the regions of the ascending aorta 50 and coronary ostium 52 wherein those sections of the catheter 30 normally reside during in situ placement.

It will be appreciated that various modifications, additions and alterations may be made to the preferred embodiments which are shown and described herein. Accordingly, it is intended that all such additional embodiments and modifications, additions and alterations to the herein described embodiments may be included within the scope of the following claims.

What is claimed is:

1. A left coronary artery guiding catheter, comprising:
   a) an elongate tubular catheter body having a distal end, a proximal end, a port in the distal end and at least one inner lumen extending longitudinally therein to the port in the distal end;
   b) a longitudinal axis extending longitudinally through said catheter body;
   c) a distal portion of said catheter body having at least three curvatures formed therein, each said curvature being in substantially the same plane, said three curvatures comprising;

a primary curved section at angle P in FIG. 6, of 15° to 45° in a first direction, having a midpoint;

a secondary curved section at angle S in FIG. 6, of 55° to 85° in a second direction, having a mid-point and being located proximal to said primary curved section; and a tertiary curved section at angle T in FIG. 6, of 85° to 115° in the same direction as said secondary curved section, having a mid-point and being located proximal to said secondary curved section; and d) an intermediate section of said catheter body extending between the mid-point of said secondary curved section and the midpoint of said tertiary curved section, having substantially less curvature than either the secondary curved section or the tertiary curved section and having a length of about 1.5 cm to about 3 cm, said length being greater than a length of a distal section which extends from the mid point of the secondary curved section to the midpoint of the primary curved section.

2. The guiding catheter of claim 1 wherein the distal end of said catheter body is formed of material which is softer than the remainder of said catheter body.

3. The guiding catheter of claim 2 wherein the distal end of said catheter body is formed of material having a Shore D durometer hardness of 33+/−5 while the remainder of said catheter body is formed of material having a Shore D durometer hardness of 63+/−5.

4. The guiding catheter of claim 1 wherein the portion of said catheter body extending between the mid-point of said secondary curved section and the mid-point of said tertiary curved section is approximately 2.5 cm in length.

5. The catheter of claim 1 wherein the length of the intermediate section of the catheter body is substantially greater than the length of the distal section.

6. A method of percutaneously inserting and positioning a tubular guiding catheter in the left main coronary artery of a human being, said method comprising the steps of:

a) providing a left coronary artery guiding catheter comprising:

an elongate tubular catheter body having a distal end, a proximal end, a port in the distal end and at least one inner lumen extending longitudinally therein to the port in the distal end and a longitudinal axis extending therethrough;

a distal body portion having formed therein in substantially the same plane a primary curved section at angle P in FIG. 6 having an angle of curvature in a first direction and a midpoint, a secondary curved section at angle S in FIG. 6 having a midpoint and being located proximal to said primary curved section with an angle of curvature larger than the angle of curvature of the primary curved section and in a second direction opposite the first direction, and a tertiary curved section at angle T in FIG. 6 having a mid-point and being located proximal to said secondary curved section with an angle of curvature larger than the curvature of the secondary curved section and in the same direction as said secondary curved section, and an intermediate catheter body portion extending between the midpoint of the secondary curved section and the midpoint of the tertiary curved section, having substantially less curvature than either the secondary curved section or the tertiary curved section and having a length of about 1.5 cm to about 3 cm, said length being greater than a length of a distal section which extends from the mid point of the secondary curved section to the midpoint of the primary curved section;

b) inserting said catheter, distal end first, into the vasculature;

c) advancing said catheter through the ascending aorta to a point where the tertiary curved section of said catheter is positioned high in the proximal aortic root;

d) further advancing said catheter, with concomitant counterclockwise rotation, until the distal end of said catheter engages the left coronary ostium; and e) subsequently retracting said catheter to a point where said tertiary curved section is in abutment with the aortic wall contralateral to said left coronary ostium such that the intermediate catheter body portion traverses the lumen of said aorta.

7. A left coronary artery guiding catheter comprising:

an elongate tubular catheter shaft having a distal end, a proximal end, a port in the distal end and at least one inner lumen extending longitudinally therein to the port in the distal end and a longitudinal axis extending there through;

a distal shaft portion having formed therein in substantially the same plane a primary curved section at angle P in FIG. 6 having an angle of curvature in a first direction, a secondary curved section at angle S in FIG. 6 having a mid-point and being located proximal to said primary curved section with an angle of curvature larger than the angle of curvature of the primary curved section and in a second direction opposite the first direction, and a tertiary curved section at angle T in FIG. 6 having a mid-point and being located proximal to said secondary curved section with an angle of curvature larger than the curvature of the secondary curved section and in the same direction as said secondary curved section; and an intermediate catheter shaft section extending between the midpoint of the secondary curved section and the midpoint of the tertiary curved section, having substantially less curvature than either the secondary curved section or the tertiary curved section and having a length of about 1.5 cm to about 3 cm, said length being greater than a length of a distal section which extends from the mid point of the secondary curved section to the distal end of the catheter body.

8. The left coronary guiding catheter of claim 7 wherein the angle of curvature of the primary curved section is about 15° to 45°.

9. The left coronary artery guiding catheter of claim 7 wherein the curvature of the secondary curved section is about 55° to 85°.

10. The left coronary artery guiding catheter of claim 7 wherein the curvature of the tertiary curved section is about 85° to 115°.

* * * * *